United States Patent [19]

Southwell

[11] Patent Number: 4,560,381
[45] Date of Patent: Dec. 24, 1985

[54] DISPOSABLE PANTY FOR MENSTRUAL WEAR

[76] Inventor: Sandra R. H. Southwell, 1014 E. Pueblo, Phoenix, Ariz. 85020

[21] Appl. No.: 511,470

[22] Filed: Jul. 7, 1983

[51] Int. Cl.$^4$ ............................................. A61F 13/16
[52] U.S. Cl. ........................................ 604/396; 2/406
[58] Field of Search .............. 604/396, 397, 391, 394; 2/406

[56] References Cited

U.S. PATENT DOCUMENTS

| | | | |
|---|---|---|---|
| 2,102,359 | 12/1937 | Frieman | 2/406 |
| 2,144,728 | 1/1939 | Paul et al. | 604/396 |
| 2,515,737 | 7/1950 | Schwarzberger | 604/394 X |
| 2,748,772 | 6/1956 | Titone et al. | 604/396 |
| 3,038,474 | 6/1962 | Harwood et al. | 604/397 |
| 3,424,162 | 1/1969 | Parravicini | 604/396 |
| 3,489,149 | 1/1970 | Larson | 604/394 |
| 3,520,304 | 7/1970 | Kubali et al. | 604/396 |
| 3,599,638 | 8/1971 | Rickard | 604/396 |
| 3,613,686 | 10/1971 | De Woskin | 604/396 |
| 3,653,381 | 4/1972 | Warnken | 604/391 |

*Primary Examiner*—William H. Grieb
*Attorney, Agent, or Firm*—Weiss & Holloway

[57] ABSTRACT

The invention shows a protective, lightweight, disposable woman's hygienic panty for removeably carrying a feminine napkin during a woman's menstrual cycle or period. A relatively thin, lightweight, disposable, biodegradable, mesh-like outer panty shell is affixed to or contiguous with a relatively thick inner layer of absorbent material operably disposed about the inner surface of a lower body portion proximate at least the lower one half of the panty. Alternately, an inner shell or liner of relatively thick absorbent material having a pad-receiving depression can be fitted, temporarily or permanently, into ordinary menstrual panties or common panties or briefs. An elongated, nearly rectangular depression or indentation having oval end portions is included or formed in the relatively thick layer for carrying, aligning, or positioning a feminine napkin. The feminine napkin-shaped depression carries or positions the feminine napkin for use during the menstrual period and provides for easy removal when the napkin is soiled. The panty or liner may be discarded after a single use such as after a heavy discharge or several lightly soiled feminine napkins may be discarded before the entire panty or liner is thrown away. The invention contemplates a waist adjustable version and a one-size-fits-all version utilizing side slits and fasteners along the slits to enable substantially all sizes of women to use a single protective panty in accordance with the present invention.

59 Claims, 15 Drawing Figures

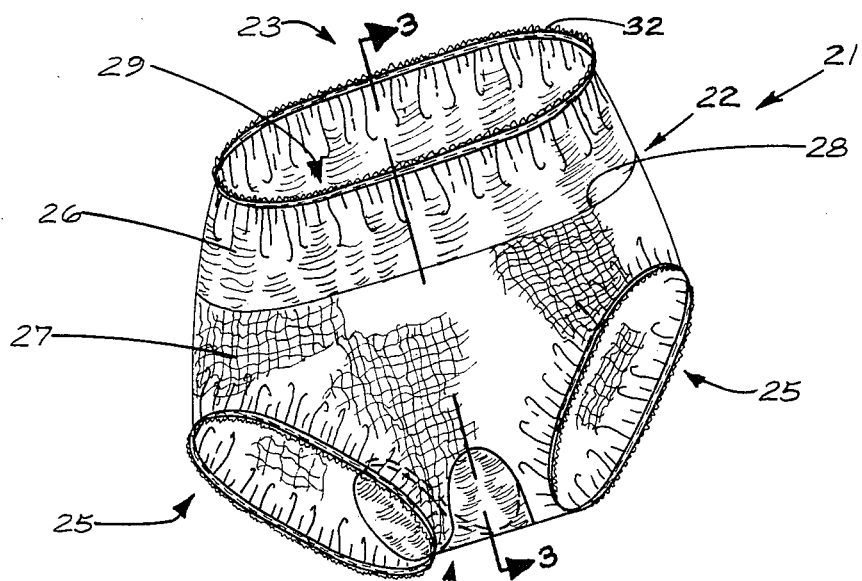
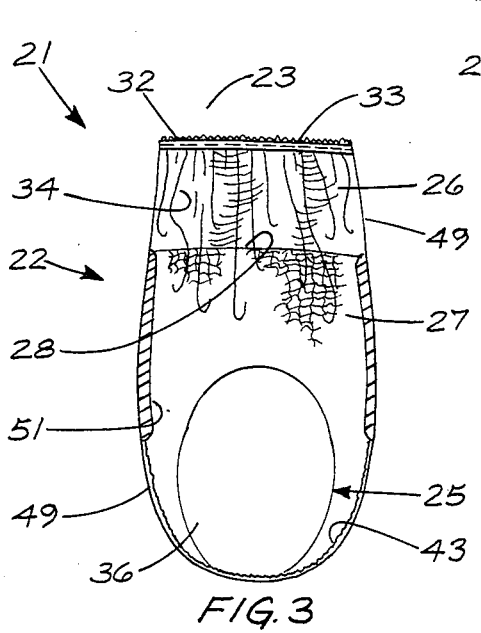
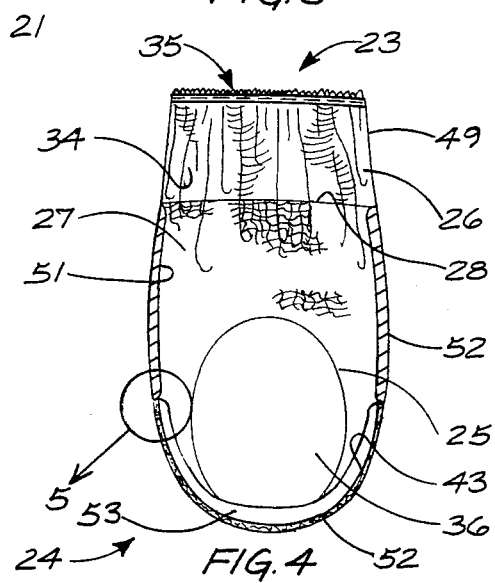
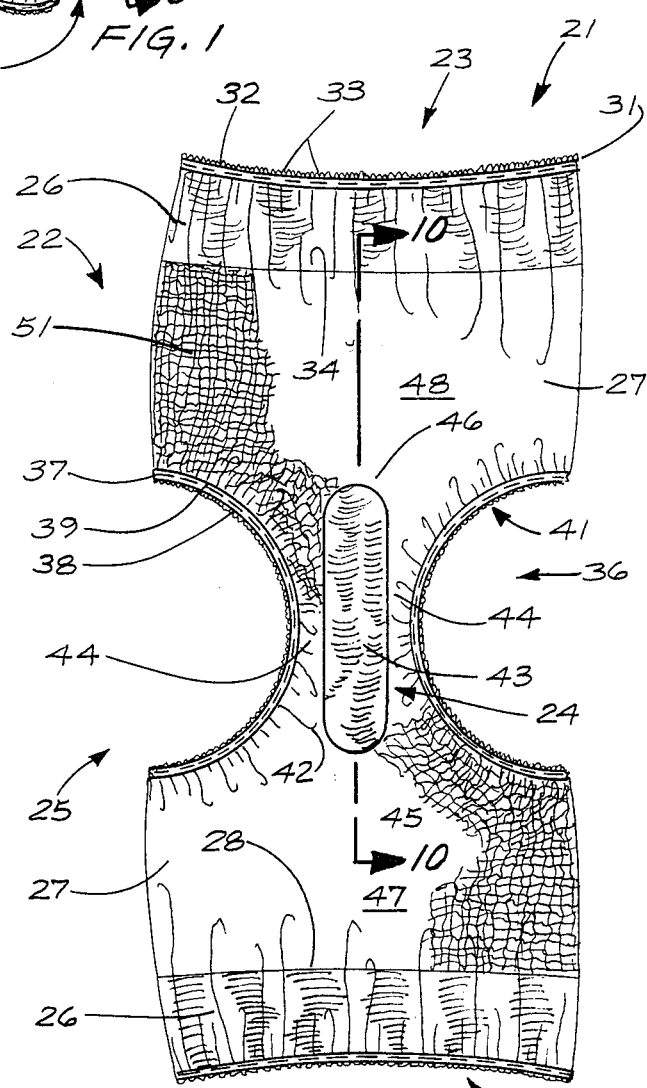
FIG. 1
FIG. 2
FIG. 3
FIG. 4

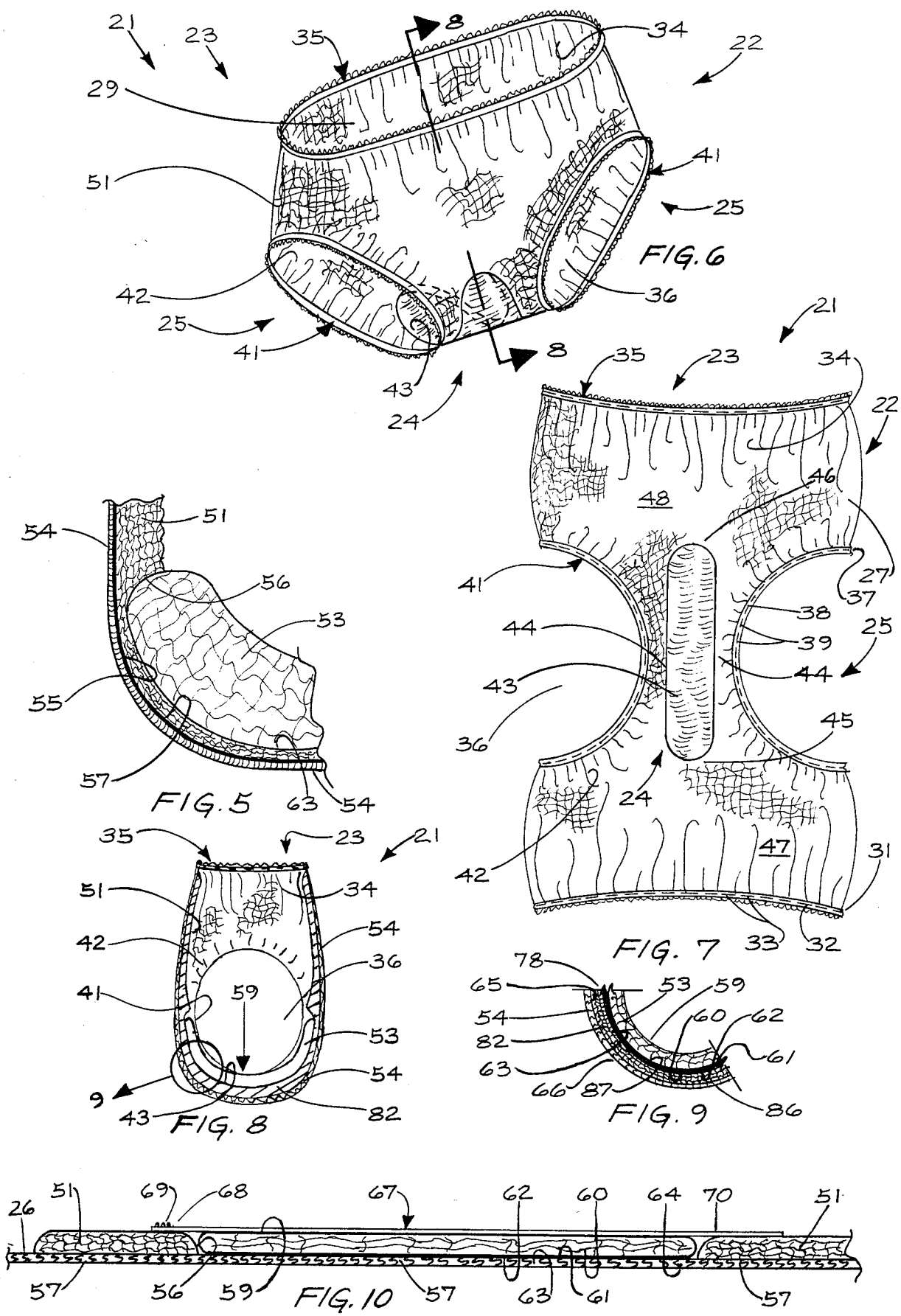

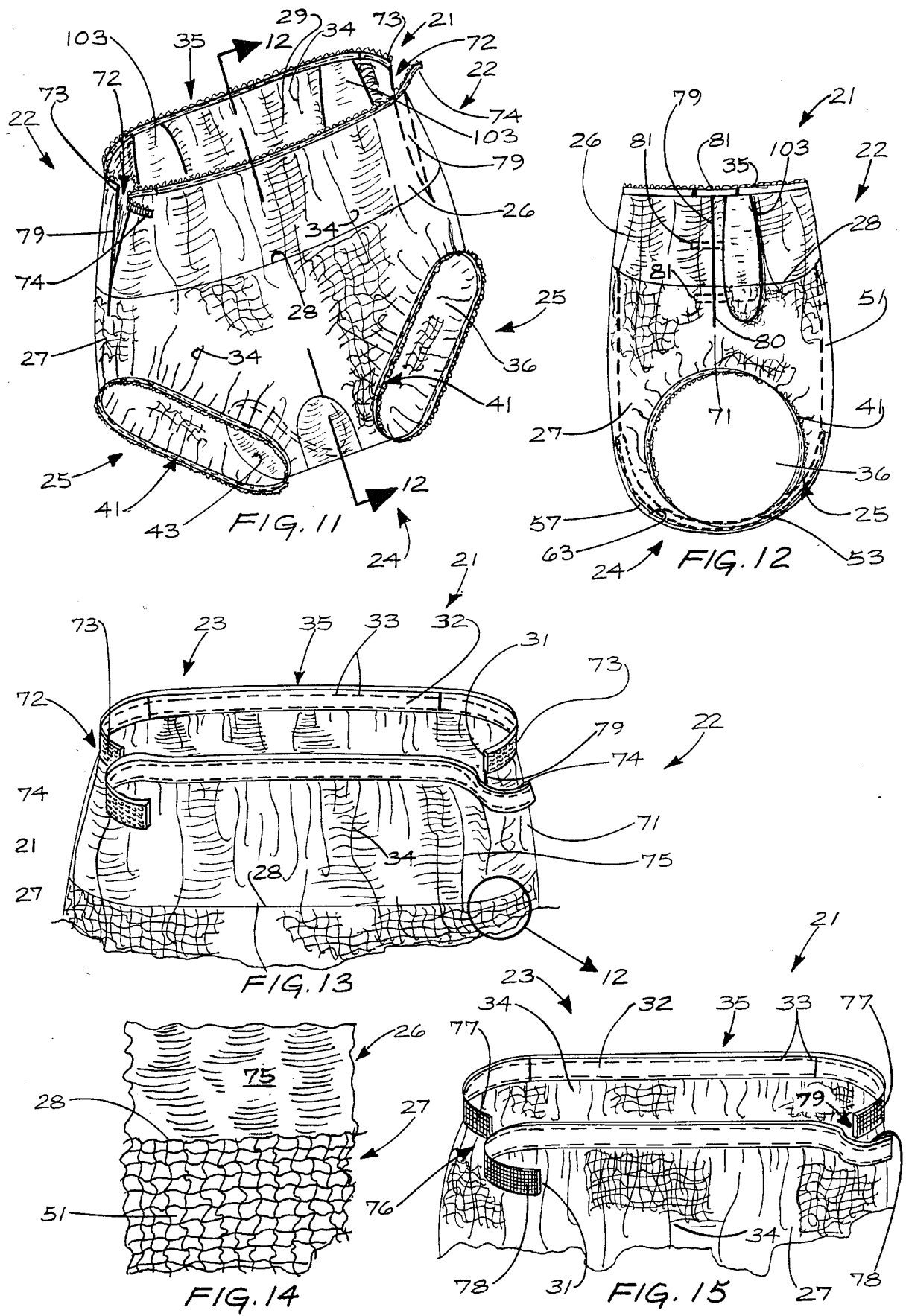

DISPOSABLE PANTY FOR MENSTRUAL WEAR

BACKGROUND OF THE INVENTION

1. Field of the Invention

The present invention relates to a disposable panty for menstrual wear and more particularly to a disposable panty which includes a top portion of lightweight disposable material and a bottom portion including a disposable absorbent layer of relatively low-cost cellulose framing with an elongated depression disposed generally in the central crotch area for receivably positioning any type of feminine sanitary napkin therein.

2. Description of the Prior Art

Disposable diapers have been, in general, used for over two decades and those used today usually include a plurality of layers including thin sheets of flexible plastic-like material that are moisture-proof or impervious, for example, polyvinyl chloride, a polyethelyne film, a woven hydrophobic fabric, or some similar moisture-proof material. These are usually alternated or combined with layers of fleece-like cellulose often reinforced by parallel threads and often including cotton gauze, or the like to provide a light, fluffy, absorbent material and many of todays disposable diapers are truly disposable in the sense that they are biodegradable and all portions of the diaper will degrade, rot or decay over time.

The evolution of women's garments for wear during their menstrual cycles has been much slower. For years, the standard article of clothing during the menstural period was the belt or strap for holding a feminine pad or feminine napkin as shown in U.S. Pat. No. 3,038,474. This system was extremely uncomfortable, awkward to put on and take off, awkward to change pads, usually left visible belt or strap marks or lines through the outer garments, was often messy or leaked due to improper fitting or alignment problems or a particularly heavy discharge causing soiled or stained panties and possibly soiled outer garments. Due to all these problems, most women had no confidence in the belts and absolutely no feeling of security. However, there was no other choice during most of this time period other than switching to a tampon which was not suitable for many women and young girls, which many women could not wear for health reasons or the like including the chance of toxic syndrome, and which was very unreliable during periods of heavy discharge. Furthermore, the tampon string causes wicking which can draw the discharge and cause moisture staining of undergarments and outer garments which often results in embarrassment.

As the feminine napkins or pads continued to be more realistically disposable, some women turned to ordinary panties or a panty with a reinforced crotch portion and simply wore the pad in the crotch area. This usually led to misalignment and pad movement which caused seepage, leakage and a general soiling or staining of the ordinary panties and proved unsatisfactory and often embarrassing for many women.

The next step in the evolution of menstrual wear was the washable panty specifically designed for use with a feminine pad. An example of this type of panty is illustrated in U.S. Pat. No. 3,489,149. This patent teaches a panty-type garment for use primarily during the female menstrual cycle or period and the garment is made from a stain-resistant washable fabric such as polyolefin and includes a small pocket in the crotch area of the garment for carrying a disposable pad which is disposed, or positioned in the pocket, and can be readily removed and replaced with a fresh pad, if necessary. One side of the pocket is formed by the crotch portion of the panty while the other side is formed from at least one but preferably two layers of woven hydrophobic fabric having a nap on at least one side with the nap positioned so as to lie against the skin of the user which tends to provide a wicking action to transfer liquid from one side through the interstices of the material to the underside leaving the skin side relatively dry and comfortable. The second layer is placed with the nap surface away from the first layer and tends to retain the moisture and may be sufficient on days when the flow is light or spotty, as is in the case for many women during most of the female menstrual period. During days of heavy menstrual flow, the absorbent pad is inserted into the crotch pocket to absorb the excess moisture which the second layer of fabric laminate cannot retain. Since the garment is made from washable material, it is intended that it be washed and reused from time to time as required. Because the pad may not be inserted into the pocket at the particular time when a heavy discharge occurs, the discharge can flow readily through the woven hydrophobic fabric or out the sides or ends and out to the crotch portion of the panty staining the panty and potentially causing a messy embarrassment. Furthermore, since the top of the pocket is the very material absorbing the initial menstrual flow, it may be quite difficult, distasteful and unsanitary to remove and change pads. Yet further, washing can prove difficult due to the very nature of the semi-waterproof nap on the fabric and since the pocket is designed for a relatively tight fit, it cannot handle today's many different thicknesses, sizes and lengths of feminine napkins.

Disposable panties were further developed and initially included only a reinforced crotch portion such as that shown in U.S. Pat. No. 3,424,162. This patent teaches a hygienic panty including a body portion which is at least partially formed of a cellulose material in a fleece-like form. While the panty is disposable and includes a fleece-like interior lining, it does not contain a means for positioning or securing a feminine napkin in place during wear and/or use. Therefore, the hygienic panty and pad tends to leak or seep around the side portions of the crotch area or in front of or in back of the feminine pad or the pad itself may shift during a heavy discharge and cause considerable leakage, mess and embarrassment.

Menstrual panties were then developed wherein the crotch area contained a piece of flexible material such as thin plastic having the characteristic of impenetrability by liquid or impermeability to ensure against passage of the menstrual discharge to the outer wall of the crotch portion of the panty. The pad or napkin was held in place by an inner wall which formed the top of a pocket enclosed on at least three sides, and after the napkin became soiled, the entire panty garment was disposed of or thrown away. This is taught in U.S. Pat. No. 2,748,772. Furthermore, U.S. Pat. No. 3,599,638 shows a disposable panty having an open mesh construction with an applique of fine cotton fibers adhesively bonded to at least one side thereof. At least one inner and preferably two auxiliary layers of absorbent material are disposed over the crotch area of the panty on the inner surface thereof and secured to the crotch area formed by the leg openings so that the auxiliary layer cooperates with the crotch area to form a pocket or receptical for a sanitary napkin. Again, the panty uses a pocket design for holding the napkin while it provides a means for changing from a first soiled napkin to a second napkin. It is also designed to be thrown away after use.

Many of the problems arising from the menstrual panties of the prior art include soiling or staining of the panty or outergarment including a dress, skirt, slacks, shorts or the like which a women is wearing at the time; the rather heavy, ugly, bulky look or impression, real or imagined, created in the eyes of the average woman; the lack of a thin, lightweight, feminine-type garment capable of serving the present purpose; the weight and feel of the material; the complete lack of any feeling of real security; the total lack of 100% protection from stains, leakage, embarrassment and the like; the lack of true disposability; the lack of a biodegradable panty; particular problems arising during athletic activities, when traveling, sitting for long periods of time, either in an office, watching spectator sports, at home and the like; a single panty for both day and night usage; leakage and seepage both through and around the pad due to the wick action in the panty, unusual exercise, or the like and the lack of adequate protection or absorbent material disposed around the pad position; the lack of an acceptable panty insert, either removeable or with means for securing it inside a panty; a panty which is provided in small medium, large and extra large sizes; a panty which has an adjustable waist to fit several different sizes of women; a one-size-fits-all panty; a panty designed for hospital applications and the like; a panty capable of handling today's modern very thin panty shield-type pads, regular pads, medium pads, thick pads, wide pads, longer pads, and for handling all such pads with or without a tampon; particular problems during a heavy discharge as opposed to the remaining portion of the menstrual cycle yet being able to also accommodate the normal spotting occurring during most of the menstrual period and times of light discharge as well. Furthermore, today's women require panties which do not show the outline of the panty lines at the waist and legs, at the seams up the sides, and which do not show the bulky or heavy look in the crotch area during their period. Yet further, today's women desire to wear one or more of full size panties, partially sized panties, hip-hugger panties, bikini panties, and the like.

The disposable panty for menstrual wear of the present invention solves virtually all of the above problems and avoids all of the disadvantages thereof by providing a simple, lightweight, disposable panty or panty liner which can be used with any of today's feminine pads from very thin to very thick or with custom-made or especially designed pads having their length and/or width and/or thickness modified, and all can be accommodated without mess, fuss or trying to remove and insert pads into possibly messy pockets, etc. in very feminine-like garments which provide a complete feeling of security and protection with fashion and style.

SUMMARY OF THE INVENTION

The present invention teaches a disposable woman's protective menstrual panty for holding a feminine napkin. A relatively thick layer of disposable absorbent material is provided with a depression including a substantially thinner layer of disposable absorbent material operably disposed longitudinally in the crotch area of the panty and extending at least partially upward in both the front and rear portions. The depression means is dimensioned for retainably receiving a feminine napkin therein for positioning same during use.

The protective panty of the present invention may be used with any size, type or shape of outer panty shell or covering and with any size, type or shape of feminine napkin. The panties are adapted to be waist-adjustable or fully adjustable to enable one size panty of the present invention to fit relatively all size women. The top portion of the panty may be made from a relatively very thin mesh-like material which covers only the top portion and is affixed to the lower portion containing the relatively thick layer of absorbent material or, preferably, the relatively thin layer forms an outer panty shell for the entire panty and the lower portion is lined with the relatively thick absorbent layer containing the depression which includes an elongated feminine napkin-shaped indentation extending along the axis of the crotch area and disposed for receiving a feminine napkin therein for positioning and aligning the napkin during use.

The invention also contemplates, as an alternate embodiment, a lightweight, absorbent panty liner adapted to be operatively disposed within a woman's conventional panty, a menstrual panty, a thin outer shell-like panty-shaped layer and the like. Unlike the liner which can be worn with a conventional panty, the menstrual panty of the present invention is a separate garment and is not meant to be worn with another panty. The panty liner includes the same relatively thick disposable layer of absorbent material shaped at least like the bottom half of a conventional panty and including a depression disposed proximate the longitudinal crotch axis. The depression includes an elongated, feminine napkin-shaped indentation whose width is symmetrically disposed on the axis between the panty leg openings and the sides of the indentation and longitudinally extends along the axis at least one third of the way up the front and back portion thereof for absorbing substantially all seepage, leakage, discharge moisture and the like escaping from and around the pad to prevent stains, embarrassment, and the like. The elongated napkin-shaped indentation operatively receives a feminine napkin therein for positioning same, proximate the vaginal area of the user and the layer of absorbent material is operably disposed within the bottom portion of the panty, panty-like shell or the like for converting it into an absorbent menstrual panty.

Further, both the menstrual panty and panty liner of the present inventions may be packaged for sale with a feminine napkin inserted or placed within the elongated indentation, either loosely, sealed therein with the tape strips on the bottom of the pads, or loosely secured therein by a tear tab strip disposed over the top portion thereof. Both the menstrual panty and the panty liner of the present invention may be worn without a feminine napkin, at least during the light or spotty days of a womans's period. However, the preferred usage is with a pad and the panty and/or panty liner serving as a back-up or as added protection. Any size of pad may be used including a custom designed pad for one or both of the menstrual panty and the menstrual panty liner of the present invention and the height of the relatively thick layer of absorbent material within the panty, in both the throw-away panty design and in the throw-away liner design, may be varied from approximately one half the way up the panty to as high as the waistband thereof depending upon the use to which it is put, the size and shape of the panty involved, and the like. Similarly, the thickness of the various portions of the panty and the liner may be varied, as desired, and waterproof inserts and the like may or may not be inserted, as desired.

Other advantages and meritorious features of the present invention will be more fully understood from the following detailed description of the drawings and the preferred embodiment, the appended claims and the drawings which are described hereinbelow:

BRIEF DESCRIPTION OF THE DRAWINGS

FIG. 1 is a perspective view of a full size, disposable, menstrual panty of the present invention;

FIG. 2 is a top plan view of the panty of FIG. 1 split down the side seam and opened up along its longitudinal axis;

FIG. 3 is a sectional side view taken along view lines 3—3 of FIG. 1 and illustrating an alternate embodiment of a panty liner incorporating the inventive concept of the present invention;

FIG. 4 is a sectional view of the panty as in FIG. 3 with a feminine pad inserted;

FIG. 5 is a blown-up portion as illustrated within the circle labelled "5" of FIG. 4;

FIG. 6 is a hip-hugger type panty embodiment of the present invention;

FIG. 7 is a top plan view of the panty of FIG. 6 cut down the sides and opened up along the longitudinal axis thereof;

FIG. 8 is a sectional side view taken along view lines 8—8 of FIG. 6;

FIG. 9 is a blown-up view of that portion contained within the circle labelled "9" of FIG. 8;

FIG. 10 is a sectional side view taken along view lines 10—10 of FIG. 2;

FIG. 11 is a perspective view of a full size, one-size-fits-all embodiment of the present invention;

FIG. 12 is a side view of another embodiment of the panty of FIG. 11;

FIG. 13 is a partial perspective view of the panty of the present invention having an adjustable waist portion;

FIG. 14 is a blown-up view of that portion of FIG. 13 shown within the circle labelled "14" of FIG. 13; and FIG. 15 is an alternate embodiment to the panty of FIG. 13 showing a different means for fastening at least the waist portion thereof to adjust the panty to various sized women.

DETAILED DESCRIPTION OF THE PREFERRED EMBODIMENT

The disposable panty of FIG. 1 illustrates the preferred embodiment of the present invention. In FIG. 1, the panty 21 is depicted as a full size panty although any type or size of panty including a hip-hugger, a bikini-type panty, a brief-type panty, a band-legged brief panty and the like can be used with the concept of the present invention. The disposable, hygienic, menstrual panty 21 includes a body portion 22, a waist portion 23, a crotch portion 24, and leg portions 25. The body portion 22 is usually divided into a top portion 26 and a bottom portion 27. In the preferred embodiment, the top portion 26 includes a lightweight, disposable, bio-degradable, open mesh-type material or fabric made at least partially from a wood fiber or cellulose material, a cellulose material reinforced by a number of parallel threads or a criss-cross of threads or of a paper-like, relatively thin, tear-resistant material or the like.

The bottom body portion 27 may be totally separate from the top body portion 26 and sewn together or otherwise sealed as at seam or division line 28. The exterior of the panty 21 of FIG. 1 may include a thin shell or outer layer 49 of the same type of mesh-like material as the top portion 26 with the bottom portion 27 differing only in the interior thereof. Alternatively, the outer layer of the bottom portion could be made from a cellulose or partially cellulose material or a non-woven cross-threaded fabric having on open mesh construction or a pair of layers of woven hydrophobic material having a nap on at least one side with the nap positioned so as to lie inwardly on the inside to provide a wicking action to transfer moisture from the inside through the interstices of the material to the underside leaving the skin side feeling relatively dry and comfortable with the second layer being placed with its nap surface away from the first layer so as to retain any moisture passing through the first layer therebetween. Alternatively, an extremely light, thin, plastic-like layer impervious to water or liquid may line the outside and/or the inside of th lower portion 27, if desired, or a plain menstrual panty or an ordinary panty could be permanently or removeably lined with gauze-like layers or other disposable, absorbent material, modern sanitary napkin fibers, cellulose material (woven or loose) and the like. Regardless of the particular material used, an extremely lightweight, relatively inexpensive, easy-to-manufacture, comfortable, menstrual panty which requires no washing and can be thrown away after several uses or after a single use, as desired or required, will be made according to the teachings of the present invention. As used herein, the term panty means menstrual panty of the present invention unless the contrary is clearly indicated, as with the term conventional panty.

The lower body portion 27 includes on its inside or inner surface a relatively thick layer 51 of partially or totally cellulose material 51 which is in a compressed fleece-like or absorbent pad-like form to provide a relatively smooth, substantially flat surface on the interior of the bottom portion 27 of the panty 21 which is highly absorbent and retains moisture or liquid. Fine fibers may be cross-threaded or linked to form a non-woven, cross-threaded fabric having an open mesh construction and an applique of fine cotton may be adhesively bound to the inside surface in a random manner such as by air blowing or the like. Spaced warped threads and spaced fill threads running perpendicular to each other may be adhesively bonded together and the threads may be cotton, rayon, nylon, or the like, any of which can form the backing for the fine cotton-like fleece or gauze-like material or absorbent pad-like material lining the inner surface of the lower or bottom body portion 27. It is important to realize that the relatively thick layer 51 of gauze-like or cotton-like fleece material covers substantially the inner surface of the entire lower body portion 27, is substantially highly moisture absorbent and is capable of acting as a back-up for a primary feminine napkin or pad at least during periods of light or moderate discharge or spotting.

Referring to FIGS. 1 and 2, the waist portion 23 includes a body opening 29 for putting on and taking off the panty 21 and an extremely thin, preferably flat, ribbon-like elastic band or rubber band 31 extending completely around the waist portion 23 and preferably covered with a thin layer of fabric or reinforced fabric 32 and sewn on or otherwise affixed to the top edge of the top body portion 26 while the elastic band or ribbon 31 is stretched and then released after sewing to produce the folds or pleats 34 to allow expansion of the panty body as well as the elastic band 31 so that the disposable panty 21 can fit various sized women. In the preferred embodiment, the relatively flat ribbon 31, the top edge of the top body portion 26, and the overlaying fabric 32 and stitches 33 are designed to form an extremely thin waistband 35 to the disposable or throwaway panty or undergarment 21 so that relatively no tell-tale panty line, waistband, or seam line is visible through the wearer's outer clothing.

The leg portions 25 of the disposable panty 21 include a generally circular or oval leg opening 36 surrounded by a relatively thin elastic ribbon or rubber band-type elastic strip 37. The elastic ribbon 37 is secured proximate to the outer edge portion of the underlying material of the lower bottom body portion 27 to outline or define the leg opening 36. The elastic ribbon 37 or the elastic ribbon 37 and the outer edge portion of the lower body portion 27 may be covered with a thin layer of reinforcing fabric which is sewn or otherwise affixed or attached as by thread or stitches 38. Again, the elastic ribbon 37, the reinforcing fabric 38, the upper edge portion of the lower body portion 27 and the stitching 39 are relatively flat and thin so that they do not present any tell-tale panty lines or broadcast or telegraph the presence of an undergarment let alone a disposable hygienic menstrual panty through the women's outer clothes or garments regardless of whether she is wearing slacks, relatively tight jeans, shorts, athletic clothes, or the like. Furthermore, as with the waistband 35, the leg bands 41 are stitched or otherwise secured with elastic member 37 stretched so that when the elastic ribbon 37 is released after sewing, the pleats or folds 42 produced are to enable both the leg band 41 itself and the fabric or material adjacent thereto to expand to accomodate relatively larger legs for larger size women, as desired.

The crotch portion 24 of the disposable hygienic panty 21 of the present invention includes an elongated, generally rectangular indentation 43 having oval-shaped end portions 45, 46 formed in the relatively thick, absorbent material covering 51 coating or lining the entire inside surface of the shell 52 of the lower body portion 27 of the panty 21. The cellulose material is preferably in a loosely woven, absorbent form to provide a light, fluffy, smooth, absorbent layer or layers which cover the entire inner surface of shell 52 of the lower body portion 27 including the inside front surface 47 and the inside rear surface 48 from the rear seam or division line 28 to the front division line 28 as will more fully be described hereinafter. The elongated indentation or depression 43 of the crotch portion 24 is surrounded along both of its longitudinal sides by a relatively thick absorbent layer 51 of conventional disposable absorbent material operably disposed between the sides of the indentation 43 and the leg band 41 as indicated by reference numeral 44. Furthermore, a relatively thick layer 51 of absorbent material surrounds both the oval-shaped front and rear end portions 45, 46, respectively, of the elongated indentation or depression 43 and extends on to cover or coat both the inner front surface 47 and the inner rear surface 48 as seen in FIG. 2.

In the present application, any reference to "relatively thick" or "relatively thin" are with respect to each other. The entire disposable menstrual panty 21 of this invention is really very thin and lightweight. The thickness of the mesh-like covering of the top portion 26 is very thin, about the thickness of the leg portion of a conventional pair of nylon pantyhose, a hairnet, a silk scarf, or the like. The thickness of the inside layer 51 lining the bottom portion 27 is between substantially less than one eighth of an inch to approximately seven-eights of an inch, depending on the particular end use of the panty 21, and a range of between one-sixteenth of an inch and one inch is possible for particular applications.

FIG. 3 shows a sectional side view of the disposable panty 21 of FIG. 1 and an alternate embodiment thereto. The panty 21 shows a cross-section taken through the crotch area 24 to illustrate a side view of the elongated indentation or depression 43 extending from the central bottom portion of the crotch area 24 up to a position as high as substantially over one half way up the leg openings 36. In FIG. 3, the relatively thin, light-weight, throw-away upper body portion 26 is represented by reference numeral 26 and the outer shell, covering or outer surface thereof is indicated by reference numeral 49. Similarly, since FIG. 3 contemplates the outer shell 49 extending so as to completely encase or enclose the entire body portion 22 and crotch portion 24 of the panty 21, the outer layer of the bottom body portion 27 is also indicated by reference numeral 49 since, in this embodiment it is a single continuous sheet basically cut in the pattern of FIG. 2 and having the relatively thick absorbent material 51 on the lower body portion 27 between the seam or division lines 28 secured to the inside surface thereof by sewing, adhesion, or any conventional bonding, securing or fastening method. The inner surfaces 47, 48 of the body portion 27 is shown as including a relatively thick layer of absorbent material 51 on all inner surfaces of the lower body portion 27 including the crotch portion 24 except for that area in which a relatively thin, elongated, depression portion is disposed for forming the elongated, feminine napkin-shaped, depression or indentation 43.

In FIG. 3, the opposite side having a relatively thick layer of absorbent material 51 is not shown in the sectional view so that the indentation or depression 43 can be emphasized. Further, the outer layer of material in the crotch area 24 (see FIG. 1) is indicated by the reference numeral 49 to emphasize that a single outer coating or shell of the mesh-like material of the top body portion 26 form the entire outer layer in one embodiment of the invention. The generally elongated indentation or depression 43 is shown as extending from the lowest part of the crotch 24 up to a point approximately at least half the way up the leg opening 36 and the indentation or depression 43 is designed to operatively receive and hold or position, with or without conventional pad tape strips, any type of conventional feminine napkin or pad on the market today including the typical disposable absorbent sanitary pads or feminine napkins for menstrual use which were heretofore commonly held in place by a special strap or harnass arrangement and including all of today's variations, including custom-designed pads and the like. Many of today's pads include moisture absorbent/waterproof material such as cotton or rayon cellulose backed by a layer of PVC which is glued or otherwise coated to the underside of the pad in a very thin layer to waterproof same. The shape of the elongated indentation or depression 43 of the present invention is designed to hold or position any type, size or shape of pad including the new extremely thin panty shield-type of feminine napkins, thin pads, standard or regular feminine napkins, thick pads, the somewhat thicker maxi pads, and any size or shape of conventional feminine napkins including various lengths, widths and thicknesses. Additionally, the indentation may be customeddesigned or uniquely shaped to hold a new type pad if the manufacturer so desires. In fact, the invention contemplates a uniquely designed pad and/or a conventional pad actually packaged with or within each of the disposable panties 21, if desired.

FIG. 3 also illustrates an alternate embodiment of the present invention directed toward a lightweight, absorbent panty-liner adapted to be operably disposed, placed, located or inserted within a conventional woman's panty, a menstrual panty, a thin outer shell-like panty-shaped layer 49, and the like. The liner is a relatively thick disposable layer of absorbent material 51 shaped like at least the bottom one half of a conventional panty. A depression means is operably disposed proximate the longitudinal crotch axis of the layer of absorbent material 51 of the liner. The depression means includes an elongated feminine napkin-shaped indentation 43 whose width is symmetrically disposed on the axis between the panty leg openings 36 and the elongated sides of the indentation and whose length extends longitudinally up the front and back portions at least one third of the way from the crotch to the top of the leg openings 36. The elongated napkin-shaped indentation 43 is adapted and dimensioned to position, align or operably receive the feminine napkin or pad therein for positioning the pad proximate the vaginal area of the user. The layer of absorbent material shaped like the bottom portion of a panty is preferably an integral unit which is inserted into some type of panty or panty-shaped shell, and is (1) seated loosely therein; (2) adhered or otherwise removeably secured; and/or (3) fixedly attached or secured, as desired. If removeable, the liner and pad 53 are thrown-out after one or more uses and another liner is inserted followed by a new pad 53.

FIG. 4 shows a side view similar to that of FIG. 3 with an alternate embodiment disclosed. In FIG. 4, the outer layer or surface of the mesh-like material of the top body part portion 26 is designated by reference numeral 49, but the outer layer of material for the lower body portion 27 and crotch area 24 are indicated by reference numeral 52. In this embodiment, the two, possibly dissimilar materials, are joined together at the seam 28 and stitched or otherwise sealed, joined, bonded, or adhered together at that point to form a single unitary undergarment or menstrual panty 21. The bottom outer layer 52 may be, for example, a pair or more of woven hydrophobic fabric layers with the first having its nap disposed upwardly for absorbing and wicking moisture to draw it through the interstices of the material to the opposite side where it is captured or restrained by the second sheet of hydrophobic fabric whose nap is disposed in the opposite direction so as to render it virtually moisture proof or waterproof. This laminate of the first and second hydrophobic sheets could be used as the outer layer 52 or as a layer immediately inwardly adjacent thereto. Similarly, a thin plastic material such as PVC or a polyethylene film, both of which are substantially waterproof and impervious to leaking or the like may be used. Preferably, however, the outer shell or layer 52 is a relatively thin, lightweight, disposable, biodegradable, mesh-like material of cellulose or the like, similar to the material of the top portion 26 although any suitable lightweight, disposable cloth or paper-like material can be used.

Furthermore, the inner lining 51 of relatively thick absorbent material could include the new super absorbent nonwoven fibers used in some feminine napkins and they could be adhered, as conventionally known, to the outer layer 49 or 52 and included as part of the soft, absorbent cellulose material. The thickness of the applique or soft portion of the relatively thick layer of absorbent material 51 can be varied to produce a composite material having any desired degree of softness, bulk, feel, absorbency, and the like. Additionally, a conventional low level wetting agent could be disposed on or within the absorbent layer or layers of various other conventional types of low-cost, disposable, high-absorbency materials can be used both in the menstrual panty 21 and the liner of this invention. It will be understood that some panties may, if desired, be used with several feminine pads or napkins, particularly on light or spotty days, if desired, or discarded after a single heavy discharge or the like. Furthermore, the general type of cellulose material or fiber contemplated for use in the present invention may be a variation of that used in paper hankerchiefs, napkins, disposable diapers and the like and a paper-like mesh, material, or composite fabric for the outer covering or shell 49, 52, hereinafter referred to jointly as shell 54, may well be used such as the fabric conventionally used for throw-away dust cloths, dish towels, dish cloths and the like. FIG. 4 shows a fairly thin panty-liner type of feminine pad 53 operatively disposed within the elongated depression 43 ready for use and the formation of the indentation 43 relative to the pad 53 will be better seen in FIG. 5 which is a blown-up portion of the area within the circle "5" of FIG. 4.

In FIG. 5, the outer layer or shell of the panty is designated by reference numeral 54 indicating that it can be either the same as the single shell 49 of the upper body portion 26 or different as in the composite shell 49, 52 of FIG. 4.

FIG. 5 illustrates how the inside surface of the outer shell material 54 is lined with a relatively thick layer of absorbent material 51 and the thickness is continuous throughout most of the inside surface of the lower body portion 27 and crotch portion 24 except for the area within the elongated indentation or depression 43, as previously described. The edge of the area of relatively thick absorbent material 51 slopes outwardly toward the inside surface of the outer bottom lining 52 and forms the leading edge portion of the rear of the elongated indentation or depression 43 of the present invention. The indentation 43 formed by the tapered or distending edges 56 of the layer of relatively thick absorbent material 51 in the elongated crotch side areas 44 and the front and back crotch areas 45, 46 completely surround the indentation 43 and form or create the actual depression 43 used to hold, position and/or align the feminine pad or sanitary napkin 53 as shown in FIG. 5. The bottom surface 63 of the elongated depression 43 is shown as including a very thin layer of absorbent material 57 similar to that of the relatively thick layer of absorbent material 51. In most embodiments, this layer is disposed proximate the outer layer or shell portion 54 but in the alternate embodiment shown in FIG. 5, an intermediate plastic-like waterproof layer 55 such as PVC, polyethylene, or the like may be operably disposed between the bottom surface of the relatively thin layer 57 and the inner surface of the outer shell 54 to prevent moisture or the like from leaking or seeping therethrough due to its impermeability. Similarly, the laminate comprising first and second layers of woven hydrophobic fabric could be used instead of the plastic layer 55 with the nap of the first layer disposed upwardly toward the relatively thin layer 57 to increase wicking and the like while the nap of the opposite sheet of the laminate is disposed outwardly to retain moisture, prevent leakage and the like. In most cases, the particular material chosen for the outer layer, the particular material chosen for the relatively thick layer of absorbent material, the material chosen for any protective waterproof linings, if desired, and the like will be selected on the basis of feel, comfort, thinness, low-cost, disposability, and whether or not they are biodegradable.

FIG. 6 represents a disposable panty 21 having a body portion 22 with no top body portion 26. The entire inner lining or inner surface of the body portion 22 is lined with the relatively thick absorbent material 51 previously described and the relatively thick absorbent material 51 is removed or altered in the crotch area 24 to form the elongated indentation or depression 43 of the present invention. The rest of the panty 21 of FIG. 6 is similar to the panty of FIG. 1 and like reference numerals indicate like portions throughout this application. With the entire body portion 22 lined with the relatively thick layer or composite of absorbent material 51, the panty 21 or corresponding liner can provide even additional protection and can be used for hospital wear or the like. Although the entire disposable panty 21 of FIG. 6 is lined with the relatively thick layer of absorbent material 51, the panty 21 is nonetheless very lightweight, feminine, comfortable, and 100-percent foolproof to impart a high degree of customer confidence, trust, and the like. As with any of the disposable panties 21 or liners of this invention, the menstrual panty 21 may be worn with both the feminine pad and a tampon, if desired. It is usually necessary to use at least the disposable panty 21 of the present invention with a tampon since the string member produces a wicking action which can cause a transfer of the moisture or discharge to the outer surface of the undergarments and the like.

FIG. 7 is a top plan view of the disposable panty 21 of FIG. 6 slit down the sides and opened up so that the inside surface thereof is exposed. As in FIG. 2, previously described, FIG. 7 shows the elongated indentation or depression area 43 surrounded by the depression-defining raised areas including the area between the longitudinal side of the depression 43 and the leg opening 36 represented by reference numeral 44 and the front and rear end portions 45, 46 of relatively thick absorbent material 51 which together form or border or define the elongated depression or indentation 43. In FIG. 7, the entire inner lining of the disposable panty 21 is lined with relatively thick absorbent material 51 or disposable diaper-like or pad-like material having high absorbency, lightweight, low cost, and all of which is disposable and biodegradable. However, the extent of the relatively thick layer of absorbent material 51 from the center of the crotch area 24 or the center of the elongated depression 43 toward the waistband 35 can be varied and a top body portion of mesh-like material 26 can be added as previously described. Similarly, even on a full size panty, the thick absorbent layer 51 could line the entire inner surface of the panty, if desired, for a particular purpose such as hospital use or the like.

FIG. 8 is a sectional side view through the crotch area 24 of the panty 21 of FIG. 6 and is used to illustrate yet another embodiment of the present invention. The disposable panty 21 has a relatively thick layer of absorbent material 51 extending over the entire surface thereof up to the waistline 35 since the thickness of the absorbent material 51 in the crotch area 24 and the thickness forming the bottom 63 of the indentation 43 are both increased, it may be worn, without a feminine napkin or pad 53 during the light discharge or normal discharge portion of the menstrual period. However, the feminine napkin 53 may be placed within the elongated depression 43 formed in the thick absorbent layer 82 and secured thereto by tape strips or the like as shown in FIG. 9 during periods of heavy discharge or, if desired by the user, for added security and the like.

FIG. 9 shows that portion of FIG. 8 within the labelled circle and illustrates the outer surface 66 of outer lining 54 having an inner surface 65. Affixed to the inner surface 65 is the relatively thick layer of absorbent material 82 disposed in the crotch portion 24. The layer of relatively thick absorbent material 82 is disposed with its outer surface 86 against the inner surface 65 of the outer shell 54 while the surface 87 forms the bottom or floor of the elongated depression 43 and the relatively thick absorbent layer 82 is adapted to receive the feminine napkin 53 thereon. Many of today's feminine napkins 53 include a tape strip or adhesive strip 78 operably disposed on the lower surface 60 thereof. The adhesive side or sticky side 62 of the tape strip 78 is usually provided with a tear tap or tear strip covering the tape 78 to prevent its sticking to anything until ready for use. Once the tear tap is removed and the adhesive exposed, the adhesive surface or outside surface 62 of the tape strip 78 is selectively positioned on the top surface 87 of the absorbent material 82 and adhered thereto for firmly positioning or securing the feminine pad 53 in place during use. The upper surface of the pad 53 is operatively disposed against the women's vaginal area for absorbing relatively all menstrual flow and holding same until the pad 53 can be disposed of. As previously mentioned, the disposable panties 21 of the present invention may be sequentially used with one or more pads and only the soiled pad is discarded each time one becomes soiled, until after several pads, the menstrual panty or liner is soiled and is also discarded, but the menstrual panty or liner and pad may also be discarded after a single use, if desired, by the wearer or required by a particularly heavy discharge or the like.

FIG. 10 is a partial sectional side view of the disposable panty 21 of FIG. 2 to illustrate the longitudinal and end portions of the depression 43 and the ends 56 of the relatively thick layer of absorbent material 51 which form the depression 43. FIG. 10 also shows another embodiment wherein a relatively thin layer of absorbent material 57 is lining the elongated indentation or depression 43 as the bottom side or adhesive portion 60 of a relatively thin tape strip 78 is adhered to the top surface 63 thereof. The opposite surface 61 of the tape strip 68 is glued or otherwise secured, perhaps adhesively, to a underside 60 of the relatively thin panty shield-type feminine napkin operably disposed within the shallower elongated depression 43. Furthermore, a feminine pad may be, for example, a custom-made pad sold with and/or disposed, housed or carried in the indentation 43 of the panty 21 or liner, if desired. For example, the pad 53 is inserted within the depression 43 and secured therein not only by the raised side portions of the relatively thick layer or portion of absorbent material 51 but with or without tape strips 78 or the like but by tear-tab member or tear-strip 67 which has one end portion 68 loosely sewn or otherwise secured to the relatively thick layer of absorbent material 51 proximate one longitudinal end portion of the depression 43 such that the tear tab or covering 67 which may be operably disposed over the feminine pad 53 during storage or sale and includes an end tab or gripping tab 70 extending well beyond the end of the pad 53 and operably disposed on top of the relatively thick layer of absorbent material 51. After storage and when ready for use, the tear tab 67 is gripped by end 70 and lifted to expose the pad and then torn away from end 68 to which it is only lightly secured via stitches 69 or the like thereby removing the throw-away tear tab or covering which is used only during storage and the like and presenting the user with a ready-to-wear, disposable panty 21 or liner already equipped with a feminine napkin operably disposed within the elongated depression 43 thereof ready for use. It will be understood, of course, that while a relatively thin panty shield-type sanitary napkin 53 has been illustrated in FIG. 10, that any type of standard or conventional pad or any specially or custom-designed pad 53 could also be used. Further, it should be obvious that the tear tab covering 67 could be modified or eliminated, as desired.

FIG. 11 illustrates yet another disposable panty 21 which represents a one-size-fits-all version of the hygienic menstrual panty 21 of the present invention. In the one-size-fits-all version of the lightweight disposable panty 21 of FIG. 11, the sides 71 are slit at least one half of the way down and possibly to a portion substantially adjacent the leg opening 36 as seen in FIG. 12. Additionally, the ribbon-like elastic waistband 35 and material folds 34 permit increased expansion. Further, one or more, relatively long diaper-like folds of excess material 103 may be disposed on either side, and preferably both sides, of the menstrual panty 21 of FIG. 11 and in the rear or back panel thereof. The Velcro strip on the top back portion is extended to provide enough locking surface as the excess material is let out to fit bigger women. The side portion of the waist-band 35 is provided with a pair of Velcro pads or pads of loop-like material 73 while the inside of the extended strips of the front wasitband 35 includes the opposite Velcro portion or pad of hooks 74. The pads of loops and hooks 73 and 74, respectively, may be selectively joined at any particular location along the length thereof and removeably secured to one another to adjust the waist, belly and partially the hip size of the panties 21. In the version of FIG. 11, a single Velcro fastener 72 comprising a hook pad 74 and a loop pad 73 are operably disposed on each side of the slit 79 at the level of the waistband 35. In the embodiment of FIG. 11, the slit 79 are disposed on both side portions 71 of the panty 21 and extend approximately one half of the way down to the leg openings 36 to enable a woman to step through the opening 29 of the waistband 35 and into the panties 21 with her legs through the leg openings 36 and then adjustably fit or press the removeably attachable hook pad and loop pad together to stretch the elastic waistband portion 35 and spread or open the folds 34 to allow the waist, tummy, and hip portions of the panty 21 to be selectively adjustable for various sized women between the combination of the adjustable side openings, the elastic waistband 35 and the material folds 34.

FIG. 12 shows a sectional side view through the crotch area 24 of the panty 21 of FIG. 11 and is modified to show yet another alternate embodiment of the present invention. The disposable panty 21 of FIG. 12 again illustrates a one-size-fits-all version of the panty 21 and includes a slit 79 extending substantially down the side portion 71 to a slit end portion 80 operably disposed proximate or immediately adjacent the leg opening 36. In the embodiment of FIG. 12, three approximately equally spaced fasteners 81 are operably disposed across the slit 79 and 80 for adjustably opening and closing the slit 79 to control the fit of the panty over all parts of a person's torso which, together with the elasticity of the leg bands 41 and the folds 34, and waistband 35, provide a true one-size-fits-all panty 21. In the preferred embodiment, the fasteners 81 are Velcro pads but tape strips, and any other type of relatively flat fastening device may be used, as known in the art. Yet further, the elongated slit 79, 80 and the fasteners 81 may be provided on a single side 71 of the panty 21, if desired, but in the preferred embodiment of the present invention, both sides 71 of the disposable panty 21 include the elongated slit 79, 80 and the set of fasteners 81.

Yet further, FIG. 12 shows the relatively thick absorbent cellulose material 51 and its portion of reduced thickness comprising the bottom of the elongated indentation or depression 43 shown in FIG. 12 as housing or positioning a relatively thin panty shield-type feminine napkin which, when placed on the relatively thin bottom portion of the relatively shallow depression 43 brings the thickness of the bottom portion and the panty shield-type pad 53 approximately level with or equal in thickness to the layer of absorbent material 51 surrounding and defining the depression 43. As previously described, when a full size pad, a maxi-pad or the like, are operatively disposed within the depression 43, the top portion of the pad, usually less than 50 percent, extends upward beyond the level of the relatively thick absorbent portion 51 for a comforting and reassuring contact proximate the women's vaginal area.

FIG. 13 illustrates a waist-adjustable disposable panty 21 wherein a relatively flat elastic ribbon 31 is operably disposed within a reinforcing fabric 32 and stitched via thread 33 to form a relatively flat, substantially invisible waistband 35 which cannot be readily seen through a women's outer garments. The resulting waistband 35 is separated at the side portion 71 of the panty 21 and the outer surface of one portion 73 is provided with a Velcro pad or pad or loop-like material while the inner surface 74 of the front waistband is provided with the other portion of the velcro fastener or hook-like pad 74. When the woman steps through the opening 29 into the panty 21 and inserts her legs through the leg openings 36, she can selectively adjust the tightness or size of the elastic waistband 35 by adjustably and selectively positioning the location on the waistband 35 at which the hook portion 74 is locked or secured to the loop pad 73 in a quick release, tear tab fashion. To open, the front end containing the hook portions is simply ripped up or lifted off of or ripped off of the loop pad 73 to loosen the waist and allow the woman to step out again to change panties or the like. Both of the sides 71 of the panty 21 are substantially alike and both include Velcro fasteners, also referred to as loop pad and hook pad fasteners herein, which taken together with the elasticity of the waistband 35 and folds 34 provides a considerable degree of size adjustment to enable the fit of panty 21 of FIG. 13 to be selectively adjustable for various sized women. The use of elastic material and the fold 34 enable considerable adjustment from the elasticity alone and the open ends of the waistband portion 35 and the ability to open and shut the waistband at any of a number of selected positions by fasteners 72 provide a highly desireable waist adjustable multi-sized panty 21. Yet further, since the top body portion 26 includes a generally mesh-like or paper-like material which is relatively thin, and somewhat expandable, the mesh-like material 75 itself of the top portion 26 can expand or give for size adjustment purposes. The degree of give provided in the lower body portion 27 may be less but, if the same mesh-like material 75 is used an an outer coating with the relatively thick layer of absorbent material 51 adherred to the inside surface thereof, additional expansion is again is provided for even greater size adjustment.

FIG. 14 shows that portion of FIG. 13 enclosed within the circle "14" and illustrates the relatively lightweight, thin, disposable, mesh-like or paper-like cellulose material 75 or the like used in making the top body portion 26 of the panty 21 of the present invention. Likewise, the lower body portion 27 is shown as including the relatively thick layer of absorbent material 51 which may include, a non-woven partially or entirely cellulose material in a slightly compressed form for producing a soft outer surface; a non-woven crossthreaded support fabric having an open mesh construction and possibly including fine cross-threaded fibers forming an applique of fine cotton adhesively bound to the inside surface for absorbancy. Yet further, it may include layers or a composite of non-woven, super absorbent fibers such as used in many of today's feminine napkins or a layer of the material of the non-plastic portion of disposable diaper-like material or the like. The division line or seam 28 illustrates either the point at which the upper body portion 26 is stitched or otherwise affixed to the lower body portion 27, or alternatively, when the upper body portion material forms the shell 49 or outer covering of the entire panty 21, the boundary 28 is the vertical level above the crotch area 24 to which the absorbent material is adhered or otherwise secured to the inside portion thereof.

FIG. 15 shows another embodiment of the panty 21 of FIG. 13 where the fasteners 76 include an adhesive base 77 and an adhesive strip 78 and the fasteners 76 are operably disposed on both sides 71 of the waistband 35 of the panty 21. Again, the elasticity of the waistband 35 provides a high degree of size adjustment together with the folds 34. However, with the adhesive strips or fasteners 76 operably disposed on both sides 71 of the slit waistband 35, even greater size adjustment is possible in operation, the adhesive strip 78 is selectively positioned over the base strip 77 and operably secured thereto at the correctly fitting waist position. Alternatively, both the adhesive strip 78 and the pad 77 could be adhesive for greater adhesability and each could be covered with a conventional tear tab such as found on the bottom of a conventional feminine napkin, or on the end tabs of an elastic adhesive bandage or the like. Since the embodiment of FIG. 15 has eliminated the top body portion 26 and includes only a bottom body portion 27, the relatively thick layer of absorbent material 51 extends all the way from the crotch 24 to the waistband 35 and has somewhat less elasticity or stretchability then does the mesh-like material 75 of the top body portion 26. However, since flaps or folds 34 are provided in the material, considerable adjustment is possible between the combination of the elasticity of the waistband 35 and accompanying folds 34 and the positionability of the adhesive strips or adhesive fastening means 76.

In summary, the generally lightweight, disposable, biodegradable, hygenienic, protective women's menstrual panty for removeably carrying a feminine napkin or the like includes at least a lower body portion comprising a relatively thick layer of absorbent material forming an elongated pad-sized depression or indentation in the crotch area thereof. The depression is designed to receivably retain, align and/or position the feminine napkin in the crotch area and partially up the back and front areas adjacent thereto during use. Any type of feminine napkin can be used from the relatively new super thin panty-liner-type pads to the normal pad, thin pad, maxi pad, daytime pad, night-time pad, and the like. Furthermore, a unique pad or specially constructed pad may be used and either the specially constructed pad or normal pads can be sold within the insert of either the menstrual panty or liner of this invention as a combination. The panty is constructed so as to have an extremely flat elastic ribbon waistband, and leg band portions and extremely thin seams up the side portions to minimize the tendency of the undergarment or panty 21 to telegraph or show the outline or presence through the women's outer garments. Furthermore, many types of relatively thick absorbent materials may be used for the inner lining of at least the bottom portion of the panty including cellulose material in a non-woven form; a compressed fleece-like form; a gauze-like form; a pad material-like form; or the like such as may be air blown on and adhered to the inner surface of the outer panty; an applique of fine cotton nylon or rayon fibers adhesively bound or adhered to the inside shell surface; loosely woven or adhesively banded cotton, rayon or nylon fibers or a mixture thereof; portions of gauze or gauze-like threads, soft cotton bulk or fiber and any of the types of materials generally used as the absorbent material in disposable diapers and the like. The meshlike material or light stretchable throw-away material used for the top portion or the entire panty shown may include a woven cellulose material, a paper-like material or even a cheesecloth-type fabric or the like. Furthermore, an inner lining of fibers of the thick absorbent material may include the new super absorbent cellulose fibers used in many of today's feminine napkins.

Additionally, the panty may be provided in various sizes such as small, medium, large and extra large or in a waistband adjustable sizes or a one-size-fits-all version. In the waist size adjustment version the waistband is cut and includes tape strips or Velcro pads for selectively adjusting same while the elasticity of the waitband and the folds of fabric at the waist enable the disposable panty 21 to fit a variety of sizes of women. Furthermore, with both sides slit and fasteners along the sides, the combination of the slits, the fasteners, the elastic waistband, and the folds of material thereabout enable a single panty to fit virtually any size of woman at least from small to extra large. The same panty 21 or liner, if desired, may be used with new pads as the previously used soiled pads are discarded, the panty 21 or liner becomes soiled before disposal, or, if desired, both may be discarded together after a single use such as after a heavy discharge or the like. It will be understood that the thickness of the applique or the relative thickness of the absorbent layer can be varied to produce a composite material having the desired degree of softness, bulk, feel, security, absorbency and the like. Furthermore, the depth of the depression or indentation 43, the width of the elongation or depression 43, and the length of the elongation or depression 43 together with the shape of the end portions, from oval to rectangular and the like may all be varied, as known in the art without departing from the inventive concept of the present invention. Furthermore, the relatively thick layer may be carried from the crotch area to any place along the body of the panty 21 up to the elastic waist portion itself, if desired, but preferably, the lower body portion 27 is only extended a little over half way to the waistband for a full size panty. Likewise, for smaller or shorter panties such as bikinis, hip huggers and the like, it extends further toward the waistband, as required.

Furthermore, the panty shell or outer surface material 54 may be a one piece shell 49 or 54; a two piece unit 49 or 54, and in an alternate embodiment, a pair of conventional menstrual panties; or any type of conventional women's panties, provided each is equipped with a panty liner, fixed or removeable, and made of the relatively thick layer of absorbent material 51 and provided with applicant's elongated pad-positioning depression 43. Also, while it may be possible to wear the present panty alone or without a feminine napkin within the indentation 43, during light days and like, a pad would normally be inserted in the depression 43 for normal or spotty days and certainly for the heavy discharge days of the menstral cycle. Yet further, additional security may be obtained, if desired, by using a tampon in combination with a feminine napkin with the disposable panty 21 or panty liner 99 of the present invention for complete safety peace of mind, confidence, and comfort. The present invention has particular application to freedom from fear from menstrual problems and increased security as well as looks during travel, during participation in athletics, during any type of heavy work or exercise, and the like and it may be used for both day and night wear without fear. The disposable panty 21 and liner of the present invention are highly feminine lightweight, disposable and biodegradable undergarments capable of handling one or more feminine napkins prior to disposal while providing a look, a confidence, a peace of mind, a feeling of security, and a comfort heretofore impossible in menstrual panties or wear of the prior art.

An example of a custom designed pad would be an elongated oval-shaped or generally rectangular pad having the thickness of a panty-shield type pad or the like and designed to fit smoothly over the entire crotch area from legband to legband and up the front and back longitudinal crotch axis approximately one third of the way up to the top of the leg openings. Centered on the longitudinal crotch axis is an indentation-shaped pad-like extension of the larger oval or rectangular pads, adapted to be operably disposed into the depression for holding the larger pad in place while providing added absorbency in the crotch area.

With this detailed description of the specific apparatus used to illustrate the present invention and the operation thereof, it will be obvious to those skilled in the art that various modifications can be made without departing from the spirit and scope of the present invention which is limited only by the appended claims.

I claim:

1. A disposable woman's protective menstrual panty for holding a feminine napkin comprising:
   a relatively thick layer of disposable absorbent material; and
   a depression means in said relatively thick layer of disposable absorbent material, said depression means including a substantially thinner layer of disposable absorbent material operably disposed longitudially in the crotch area of said panty and extending at least partially upward thereof in both front and rear areas, said depression means being dimensioned for receiving said feminine napkin therein for positioning same during use.

2. The woman's protective panty of claim 1 wherein said panty is a conventional full size panty.

3. The disposable woman's protective panty of claim 2 wherein a top portion thereof may include a paper-like mesh means which is substantially lightweight, disposable, and biodegradable.

4. The disposable woman's protective panty of claim 3 wherein said top portion of paper-like mesh means substantially forms the outer shell of the entire panty to form a base for operatively disposing said relatively thick, absorbent layer on the inside surface thereof.

5. The disposable woman's protective panty of claim 1 wherein said panty is a shorter-bodied hip-hugger type panty.

6. The disposable woman's protective panty of claim 1 wherein said panty is a bikini brief-type panty.

7. The disposable woman's protective panty of claim 1 wherein one-size-fits-substantially all women.

8. The disposable woman's protective panty of claim 7 wherein said panty includes a slit down at least one side thereof and means for adjustably changing the size of said panty to ensure a comfortable fit.

9. The disposable woman's protective panty of claim 8 wherein said panty includes a slit portion down both sides thereof from the waistband to a point disposed adjacent the upper portion of the leg bands of said panty.

10. The disposable woman's protective panty of claim 9 wherein each of said two slits include at least two strips of hook and pad material for operably varying the size of the panty, one of said two hook and loop pads being operably disposed proximate the waistband portion of said panty.

11. The disposable woman's protective panty of claim 9 wherein each of said side slits include at least two tape-like adhesive strip means for selectively adjusting the size of said panty to suit the wearer, one of said two tape-like adhesive strip means being operably disposed proximate the waistband at the top of each of said slits.

12. The disposable woman's protective panty of claim 7 wherein said size adjustment means includes fastening means operably coupled to each of the side portions of said panty for selectively varying the fit of the waist thereof.

13. The disposable woman's protective panty of claim 8 wherein said size adjustment means includes at least one pair of hook and loop pads.

14. The disposable woman's protective panty of claim 8 wherein said size adjustment means includes at least one strip of adhesive-like means for selectively varying the size of said panty.

15. The disposable woman's protective panty of claim 1 further including a top portion having a lightweight, relatively thin, paper-like mesh means.

16. The disposable woman's protective panty of claim 15 wherein said top portion of paper-like mesh means forms the entire outer surface of the panty.

17. The disposable woman's protective panty of claim 13 wherein a bottom portion of relatively thick absorbent material is operatively disposed on the inside surface of said top portion from proximate the crotch area to at least one half way from the top of the leg openings.

18. The disposable woman's protective panty of claim 12 wherein a bottom portion of relatively thick absorbent material extends at least one half way from the crotch to the top of the leg openings and is operatively secured to said top portion of paper-like mesh means for forming said panty.

19. The disposable woman's protective panty of claim 1 wherein said relatively thick layer of absorbent material extends over the entire inner surface of said panty.

20. The disposable woman's protective panty of claim 1 wherein said relatively thick layer of absorbent material is sufficiently absorbent to enable said mentrual panty to be worn without a feminine napkin at least during the light or spotty days of a woman's period.

21. The disposable woman's protective panty of claim 1 wherein said depression means includes an elongated indentation in said relatively thick layer of disposable absorbent material, said disposable absorbent material surrounding said elongated indentation between the sides thereof and the leg openings of said panty and around the front and back end portions of said elongated indentation forming and defining the size and depth thereof.

22. The disposable woman's protective panty of claim 21 wherein said elongated indentation is adapted to receive said feminine napkin removeably secured therein by tape strip means operably disposed on the bottom portion of said feminine napkin, said feminine napkin being operably positionable in said elongated indentation so that approximately less than one half of the thickness thereof extends upwardly and out of said elongated indentation while the remaining portion is operably disposed therein.

23. The disposable woman's protective panty of claim 1 wherein said depression means includes means for positioning a custom designed feminine pad including a relatively wide, elongated oval-shaped layer of disposable absorbent material having a smooth continuous upper surface adapted to be disposed proximate a woman's crotch area and extending across the crotch of the panty from leg opening to leg opening and up the front and rear portions a substantial distance toward the top of the leg openings, said oval-shaped layer having the approximate thickness of a thin panty shield-type pad, the bottom surface of said oval-shaped layer including an elongated feminine napkin-shaped extension disposed the longitudinal crotch axis for being insertably received into said depression for positionally securing said oval-shaped layer and for providing added absorbency in the woman's crotch area.

24. The disposable woman's protective panty of claim 1 wherein said depression means includes means for positioning a custom designed feminine pad including a relatively wide, elongated, generally rectangular oval-shaped layer of disposable absorbent material having a smooth continuous upper surface adapted to be disposed proximate a woman's crotch area and extending across the crotch of the panty from leg opening to leg opening and up the front and rear portions a substantial distance toward the top of the leg openings, said generally rectangular oval-shaped layer having the approximate thickness of a thin panty shield-type pad, the bottom surface of said generally rectangular oval-shaped layer including an elongated feminine napkin-shaped extension disposed the longitudinal crotch axis for being insertably received into said depression for positionally securing said generally rectangular oval-shaped layer and for providing added absorbency in the woman's crotch area.

25. A lightweight, disposable, woman's protective menstrual panty for operatively receiving and positioning a feminine napkin comprising:
  a top portion of said protective panty including a lightweight, mesh-like disposable material means which operably extends downward from the waistband portion of the panty;
  a bottom portion of said panty including a relatively thick inner layer of disposable absorbent material extending at least one half of the way up the panty toward said waist portion; and
  means for operatively disposing said feminine napkin in the crotch area of said bottom inner layer for operatively positioning same, said disposing means including an elongated depression in said thick inner layer of disposable absorbent material, said elongated depression being dimensioned for receiving said feminine napkin therein for positioning said napkin during use.

26. The protective panty of claim 25 wherein said feminine napkin includes tape strip means operably disposed on the bottom thereof for removeably securing same to the crotch area of said bottom inner layer.

27. The protective panty of claim 25 wherein said top portion of mesh-like material extends downward to form a complete panty-shaped outer covering shell and wherein said bottom portion including said relatively thick layer of absorbent material is operably secured to the inner surface of at least the bottom half of said shell.

28. The protective panty of claim 25 wherein said panty is designed so that one-size-fits-all, said one-size-fits-all panty including at least one slit portion running up at least one side of the panty through the waistband and down a predetermined distance toward the leg band thereof, said at least one side slit portion including adjustably positionable fastening means for selectively varying the size of the panty and the comfort of the fit to satisfy different sized women.

29. The protective panty of claim 28 wherein said panty includes two side slits, one on each side portion thereof and fastening means operably disposed on both sides thereof for selectively varying the size adjustment of the panty for different sized women and the like.

30. The protective panty of claim 28 wherein said fastening means includes at least one hook and loop pad portion for opening and closing the slit in a tear tab manner.

31. The protective panty of claim 25 wherein said lightweight mesh-like disposable material substantially covers the entire outer surface of the panty and forms the base for securing the relatively thick absorbent inner layer thereto.

32. The protective panty of claim 25 wherein said mesh-like disposable material forms an outer covering of the top portion of the panties, and wherein said bottom portion includes a disposable backing material for forming an outer covering for the bottom portion of the panty and means for operatively joining the top and bottom portions of the panty for forming a single integral protective panty.

33. A lightweight, disposable, woman's protective menstrual panty for operatively receiving and positioning a feminine napkin comprising:

a top portion of said protective panty including a lightweight, mesh-like disposable material means which operably extends downward from the waistband portion of the panty;

a bottom portion of said panty including a relatively thick inner layer of disposable absorbent material extending at least one half of the way up the panty toward said waist portion; and means for operatively disposing said feminine napkin in the crotch area of said bottom inner layer for operatively positioning same, said relatively thick inner layer of disposable absorbent material includes said disposing means for forming an elongated indentation portion of relatively thin absorbent material extending centrally through the crotch area of said panty and at least partially up the front and back portions thereof, said indentation-forming portion being dimensioned to operably receive a feminine napkin for positioning same during use, said indentation-forming thick inner layer of disposable absorbent material which surrounds said elongated indentation being operably disposed between the longitudinal sides of said indentation portion and the leg portion of said panty, and being operably disposed around the front and back end portions of said indentation portion so as to define a substantially hollow indentation portion extending centrally through the crotch area of the panties and up the front and back thereof a predetermined portion depending upon the length of commercially available feminine napkins and the like.

34. The protective panty of claim 33 wherein said panty is a full size panty and said bottom portion including said relatively thick inner layer of disposable absorbent material extends over one half of the way up the panty from the crotch area towards the waist.

35. The protective panty of claim 34 wherein said fastening means includes at least one tape-like adhesive strip means operably disposed proximate said slit for selectively adjusting the position thereof to vary the size of the panty.

36. The protective panty of claim 34 further including means for selectively varying the waist size and fastening same to fit a particular women's size.

37. The protective panty of claim 33 wherein said panty is less than full size and said bottom portion including said relatively thick inner layer of disposable absorbent material extends approximately three quarters of the way up the panty from the crotch towards the waist portion thereof.

38. The protective panty of claim 37 wherein the waist portion includes selectively positionable fastening means for varying the size of the waist to fit different sized women and the like.

39. The protective panty of claim 33 wherein said inner layer of absorbent material is substantially thicker in the crotch area.

40. The protective panty of claim 33 wherein said indentation includes a relatively thin, at least partially absorbent, permeable covering on both longitudinal sides and on the rear end portion, with the front end open to form a pocket-like indentation for receivably retaining a feminine napkin during use.

41. A protective women's panty for removeably carrying a feminine napkin comprising:

a relatively thin, lightweight, disposable, biodegradable, mesh-like outer panty shell disposed in the shape of a woman's panty;

a relatively thick inner layer of absorbent material operably disposed about the inner surface of said outer panty shell proximate at least the lower half of said panty;

means for forming an elongated, feminine napkin-shaped depression in said relatively thick inner layer of absorbent material along the center of the crotch area and extending longitudinally up the front and rear portion of the panties, said depression being formed by said layer of relatively thick, absorbent, material surrounding said feminine napkin-shaped depression between the longitudinal sides of the feminine napkin-shaped depression and the leg bands of the panty and around the front and rear portions of the feminine napkin-shaped depression to define same;

said feminine napkin-shaped depression including means for operatively positioning a feminine napkin therein during use and providing for easy removal thereafter, at least said used feminine napkin being removed from said depression and discarded after use but usually, particularly after a heavy discharge or the like, the entire absorbent protective panty including the used feminine napkin would be discarded at one time.

42. The protective woman's panty of claim 41 wherein said panty further includes means for selectively varying the size of the panty and removeably securing same to fit substantially all normally sized women.

43. The protective woman's panty of claim 41 wherein the depth of said feminine napkin-shaped depression in said relatively thick inner layer of absorbent material is approximately more than one half of the thickness of a normal feminine napkin.

44. The protective woman's panty of claim 41 wherein the depth of said feminine napkin-shaped depression in said relatively thick inner layer of absorbent material is less than one half of the thickness of a normal feminine napkin.

45. A lightweight, absorbent, panty-liner adapted to be operably disposed within a women's conventional panty, a menstrual panty, a thin outer shell-like panty-shaped layer and the like, said panty-liner comprising:

a relatively thick disposable layer of absorbent material shaped like at least the bottom half of a conventional panty;

depression means operably disposed proximate the longitudinal crotch axis in said layer of absorbent material, said depression means including an elongated feminine napkin-shaped indentation whose width is symmetrically disposed on said axis between the panty leg openings and the long edges of said indentation and extend longitudinally along the axis at least one third of the way up from the front and back portions for absorbing substantially all seapage, leaks and discharge moisture escaping from the pad to prevent soiled garments, stains, embarrassment and the like;

said elongated napkin-shaped indentation operatively receiving said feminine napkin therein for positioning same proximate the vaginal area of the user; and said layer of absorbent material being operably disposed within the bottom portion of said panty, panty-shaped shell, and the like for converting same into an absorbent menstrual panty.

46. The panty-liner of claim 45 further including a relatively thin outer layer shaped like at least the bottom half of a conventional panty wherein said relatively thick layer of absorbent material is operatively secured to said outer layer on the inside surface thereof to form a composite outer layer-inner layer panty liner shaped like at least the bottom half of a conventional panty and adapted to be fitted therein.

47. The panty liner of claim 46 wherein said indentation includes a feminine pad operably positioned therein and packaged for sale therewith.

48. The panty liner of claim 47 wherein said feminine pad is operatively positioned within said indentation and secured therein by fastening means when packaged for sale.

49. The panty liner of claim 47 wherein a tear tab cover is operatively disposed over said provided pad with one end portion lately stitched to a portion of said relatively thick layer of absorbent material for easy tear-away purposes and the opposite end being disposed over the opposite portion of said relatively thick layer of absorbent material so that intermediate portion covers said pad within said indentation during packages and the like.

50. The panty liner of claim 46 wherein said panty liner is provided with a feminine pad in said indentation.

51. The panty liner of claim 46 wherein the outer layer of relatively very thin disposable mesh-like material at least partially contains cellulose material.

52. The panty liner of claim 45 wherein said elongated napkin-shaped indentation is formed in said inner layer of absorbent material and said composite outer-inner layer shaped like at least the bottom half of a conventional panty includes said elongated indentation and is adapted to be fitted into the interior portion of at least one of a panty and a panty-shaped outer shell means for lining at least the bottom half thereof to convert same into a relatively thin, lightweight, absorbent women's menstrual panty.

53. The panty liner of claim 52 wherein said composite outer-inner layer is adapted to be selectively removeable to be discarded with the soiled pad when desired but without discarding the panty or panty-shaped shell.

54. The panty liner of claim 52 wherein said outer-inner layer is adapted to be removeably secured within said panty or said panty-shaped outer shell means.

55. The panty liner of claim 52 wherein said outer-inner layer is adapted to be operatively positioned within said panty or panty-shaped means by means for fastening said outer-inner layer to the inside bottom portion of said panty and said panty-shaped means.

56. The panty liner of claim 45 wherein the bottom of said indentation between said outer layer and said pad includes a relatively thin indentation-lining absorbent layer including a relatively very thin impervious layer for preventing the escape of moisture through and around said pad.

57. The panty liner of claim 45 wherein said layer of absorbent material includes a relatively soft disposable absorbent cellulose material.

58. The panty liner of claim 45 wherein the relatively thick layer of absorbent material is sufficiently absorbent to enable said liner to be worn without a feminine napkin during the relatively light or spotty days of a woman's period.

59. The panty liner of claim 45 wherein said relatively thick layer of absorbent material includes a substantially thicker dimension proximate the crotch area of said panty liner.

* * * * *